(12) United States Patent
Takasu (10) Patent No.: US 9,395,334 B2
(45) Date of Patent: Jul. 19, 2016

(54) ATMOSPHERIC ENVIRONMENT MEASURING APPARATUS, ATMOSPHERIC ENVIRONMENT MEASURING METHOD AND ATMOSPHERIC ENVIRONMENT MEASURING SYSTEM

(71) Applicant: FUJITSU LIMITED, Kawasaki-shi, Kanagawa (JP)

(72) Inventor: Ryozo Takasu, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 379 days.

(21) Appl. No.: 14/018,009

(22) Filed: Sep. 4, 2013

(65) Prior Publication Data

US 2014/0007653 A1    Jan. 9, 2014

Related U.S. Application Data

(63) Continuation of application No. PCT/JP2011/058051, filed on Mar. 30, 2011.

(51) Int. Cl.
  *G01N 29/02* (2006.01)
  *G01N 5/02* (2006.01)
  (Continued)

(52) U.S. Cl.
  CPC .............. *G01N 29/022* (2013.01); *G01G 3/13* (2013.01); *G01G 3/16* (2013.01); *G01N 1/2273* (2013.01); *G01N 5/02* (2013.01)

(58) Field of Classification Search
  CPC ......... G01G 3/13; G01G 3/16; G01N 1/2273; G01N 5/02
  USPC ....................................... 73/24.06
  See application file for complete search history.

(56) References Cited

U.S. PATENT DOCUMENTS

| 5,856,198 A | 1/1999 | Joffe et al. |
| 6,208,406 B1 | 3/2001 | Nakashima |

(Continued)

FOREIGN PATENT DOCUMENTS

| JP | 06-213844 A | 8/1994 |
| JP | 09-270385 A | 10/1997 |

(Continued)

OTHER PUBLICATIONS

Japanese Office Action dated Oct. 21, 2014, issued in Japanese Patent Application No. 2013-506949, w/English translation (6 pages).

(Continued)

*Primary Examiner* — Hezron E Williams
*Assistant Examiner* — David Z Huang
(74) *Attorney, Agent, or Firm* — Westerman, Hattori, Daniels & Adrian, LLP (57) ABSTRACT

An atmospheric environment measuring apparatus including a filter disposed in a casing and adsorbing a component of a gas to be detected; a first mass sensor disposed in the casing between an inlet of the casing and the filter, including a first piezoelectric vibration element and changing a resonance frequency according to a mass of a substance adhered on a surface of the first piezoelectric vibration element; a second mass sensor disposed in a stage following the filter in the casing, including a second piezoelectric vibration element and changing a resonance frequency according to a mass of a substance adhered on a surface of the second piezoelectric vibration element; and a fan disposed in a stage following the second mass sensor in the casing and fluidizing atmosphere from the inlet toward an outlet of the casing.

9 Claims, 8 Drawing Sheets

(51) Int. Cl.
  *G01N 1/22* (2006.01)
  *G01G 3/16* (2006.01)
  *G01G 3/13* (2006.01)

(56) References Cited

U.S. PATENT DOCUMENTS

| | | | |
|---|---|---|---|
| 6,314,793 B1 * | 11/2001 | Webb | G01M 3/20 422/68.1 |
| 2002/0122177 A1 * | 9/2002 | Sioutas | G01G 17/04 356/336 |
| 2003/0035087 A1 | 2/2003 | Murayama | |

FOREIGN PATENT DOCUMENTS

| JP | 09-275055 A | 10/1997 |
|---|---|---|
| JP | 09-309329 A | 12/1997 |
| JP | 10-307115 A | 11/1998 |
| JP | 2002-333394 A | 11/2002 |
| JP | 2004-190892 A | 7/2004 |
| JP | 2004-200402 A | 7/2004 |
| JP | 2005-282908 A | 10/2005 |
| JP | 2008-032607 A | 2/2008 |
| JP | 2009-250959 A | 10/2009 |
| JP | 2009-300095 A | 12/2009 |
| JP | 2010-271285 A | 12/2010 |

OTHER PUBLICATIONS

International Search Report dated Jun. 28, 2011, issued in corresponding application No. PCT/JP2011/058051.

* cited by examiner

ATMOSPHERIC ENVIRONMENT MEASURING APPARATUS, ATMOSPHERIC ENVIRONMENT MEASURING METHOD AND ATMOSPHERIC ENVIRONMENT MEASURING SYSTEM

CROSS-REFERENCE TO RELATED APPLICATION

This application is a Continuation of PCT application No. PCT/JP2011/058051, which was filed on Mar. 30, 2011, and which designated the United States of America, the entire contents of which are incorporated herein by reference.

FIELD

The embodiments discussed herein are related to an atmospheric environment measuring apparatus, an atmospheric environment measuring method and an atmospheric environment measuring system.

BACKGROUND

In order to realize a safe atmospheric environment, it is very important to measure the atmospheric environment.

The atmospheric environment is measured at various places, whereby a generation source of harmful gases, etc. can be located.

The background art is as exemplified below.

Japanese Laid-open Patent Publication No. 2004-200402;
Japanese Laid-open Patent Publication No. 2008-32607; and
Japanese Laid-open Patent Publication No. Hei 10-307115.

SUMMARY

According to an aspect of embodiments, an atmospheric environment measuring apparatus includes a first filter disposed in a casing and adsorbing a component of a gas to be detected; a first mass sensor disposed in the casing between an inlet of the casing and the first filter, including a first piezoelectric vibration element and changing a resonance frequency according to a mass of a substance adhered on a surface of the first piezoelectric vibration element; a second mass sensor disposed in a stage following the first filter in the casing, including a second piezoelectric vibration element and changing a resonance frequency according to a mass of a substance adhered on a surface of the second piezoelectric vibration element; and a fan disposed in a stage following the second mass sensor in the casing and fluidizing atmosphere from the inlet toward an outlet of the casing.

According to another aspect of the embodiments, an atmospheric environment measuring system includes an atmospheric environment measuring apparatus including a first filter disposed in a casing and adsorbing a component of a gas to be detected; a first mass sensor disposed in the casing between an inlet of the casing and the first filter, including a first piezoelectric vibration element and changing a resonance frequency according to a mass of a substance adhered on a surface of the first piezoelectric vibration element; a second mass sensor disposed in a stage following the first filter in the casing, including a second piezoelectric vibration element and changing a resonance frequency according to a mass of a substance adhered on a surface of the second piezoelectric vibration element; a fan disposed in a stage following the second mass sensor in the casing and fluidizing atmosphere from the inlet toward an outlet of the casing; and a transmission unit wireless transmitting measured data given by the first mass sensor and the second mass sensor; and a processing apparatus obtaining the measured data transmitted from the atmospheric environment measuring apparatus via a network and measuring an atmospheric environment based on the measured data.

According to further another aspect of the embodiments, an atmospheric environment measuring method using an atmospheric environment measuring apparatus includes a first filter disposed in a casing and adsorbing a component of a gas to be detected; a first mass sensor disposed in the casing between an inlet of the casing and the first filter, including a first piezoelectric vibration element and changing a resonance frequency according to a mass of a substance adhered on a surface of the first piezoelectric vibration element; a second mass sensor disposed in a stage following the first filter in the casing, including a second piezoelectric vibration element and changing a resonance frequency according to a mass of a substance adhered on a surface of the second piezoelectric vibration element; and a fan disposed in a stage following the second mass sensor in the casing and fluidizing atmosphere from the inlet toward an outlet of the casing, a content level or a concentration of the gas to be detected in the atmosphere is measured based on measured data by the first mass sensor and measured data by the second mass sensor.

The object and advantages of the embodiments will be realized and attained by means of the elements and combinations particularly pointed out in the claims.

It is to be understood that both the foregoing general description and the following detailed description are exemplary and explanatory and are not restrictive of the embodiments, as claimed.

DESCRIPTION OF EMBODIMENTS

The conventional atmospheric environment measuring apparatus have been restricted in the installation place because of their large scales. Because of their expensiveness, it has been difficult to install the conventional atmospheric environment measuring apparatus in various places from the viewpoint of the cost. Thus, conventionally, it has been difficult to measure the atmospheric environment in a wide area without spending vast costs.

Preferred embodiments of the present invention will be explained with reference to accompanying drawings.

[a] First Embodiment

The atmospheric environment measuring apparatus, the atmospheric environment measuring method and the atmospheric environment measuring system according to a first embodiment will be described with reference to FIGS. 1 to 6.

(Atmospheric Environment Measuring Apparatus)

Figure 1:
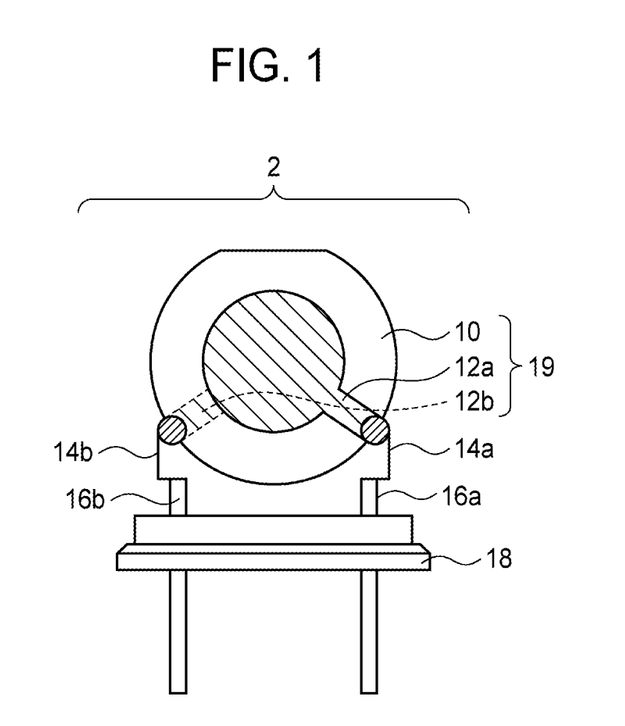
FIG. 1 is a view exemplifying a mass sensor.
Figure 2:
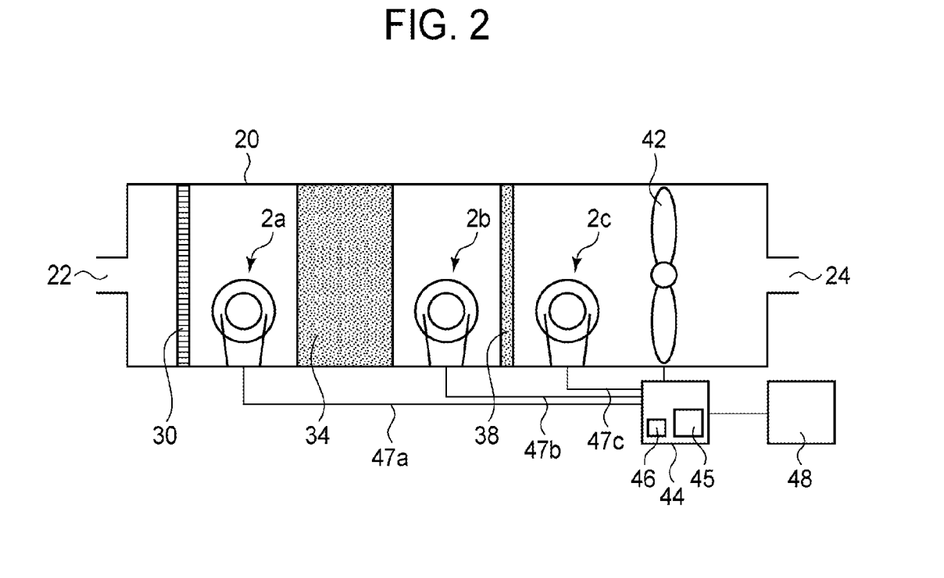
FIG. 2 is a view illustrating a construction of an atmospheric environment measuring apparatus according to a first embodiment.

First, the atmospheric environment measuring apparatus according to the present embodiment will be described with reference to FIGS. 1 to 3. FIG. 1 is a view exemplifying the mass sensor. FIG. 2 is a view illustrating the construction of the atmospheric environment measuring apparatus according to the present embodiment.

The example of the mass sensor used in the present embodiment will be described with reference to FIG. 1.

As the mass sensor, a QCM (Quartz Crystal Microbalance) sensor 2 as exemplified in FIG. 1 can be used. The QCM sensor is a mass sensor using crystal resonators and utilizes the property that when a substance is adhered on the surface of a crystal resonator, the resonance frequency of the crystal resonator changes according to a mass of the adhered substance.

The QCM sensor 2 includes a crystal substrate 10, one pair of electrodes 12a, 12b provided on both surfaces of the crystal substrate 10, terminals 16a, 16b connected to the electrodes 12a, 12b via electric leads 14a, 14b, and a support plate 18.

The crystal substrate 10 is substantially disc-shaped.

As the material of the electrodes (metal film) 12a, 12b, gold (Au), for example, is used.

The electrodes 12a, 12b and one ends of the lead 14a, 14b are connected respectively by, solder.

The crystal substrate 10 and one pair of the electrodes 12a, 12b form a piezoelectric vibration element (crystal resonator) 19.

As the substrate 10, a crystal substrate is used here, but the substrate 10 is not limited to a crystal substrate. Substrates of piezoelectric materials can be generally used for the substrate 10.

However, for the measurement of high precision, preferably, a crystal substrate is used as the substrate 10.

When a voltage is applied to the electrodes 12a, 12b via the terminal 16a, 16b, the piezoelectric vibration element 19 vibrates at a constant resonance frequency. When the substance is adhered on the surface of the piezoelectric vibration element 19, the resonance frequency of the piezoelectric vibration element 19 is lowered according to the mass of the adhered substance. A change of the resonance frequency of the piezoelectric vibration element 19 is proportional to amount of change of the mass of the substance adhered on the surface of the piezoelectric vibration element 19.

The QCM sensor 2 illustrated in FIG. 1 is provided by, e.g., KYOCERA Corporation, etc.

Next, the construction of the atmospheric environment measuring apparatus according to the present embodiment will be described with reference to FIG. 2.

As illustrated in FIG. 2, an inlet 22 and an outlet 24 are formed in a casing 20. The diameter of the casing 20 is, e.g., about 20 mm. The aperture of the inlet 22 and the aperture of the outlet 24 are set sufficiently small. The aperture of the inlet 22 is, e.g., about 4 mm. The aperture of the outlet 24 is, e.g., about 4 mm. The aperture of the inlet 22 and the aperture of the outlet 24 are set sufficiently small so as to prevent the atmosphere from flowing into the casing 20 through the inlet 22 and the outlet 24 even when a fan 42 is not being operated. As the material of the casing 20, stainless, for example, is used.

The cross sectional shapes of the casing 20, the inlet 22 and the outlet 24 are not especially restricted and can be circular or rectangular.

A mesh 30 is disposed near the inlet 22 of the casing 20. As the material of the mesh 30, stainless, for example, is used. The mesh 30 is for shutting off sands, dusts, etc. in the atmosphere.

In the stage following the mesh 30, i.e., in the downstream of the mesh 30, the first mass sensor 2a is disposed. As the first mass sensor 2a, the QCM sensor 2, for example, described above with reference to FIG. 1 can be used. On the surface of the first mass sensor 2a, various substances contained in the air which have passed through the mesh 30 can be adhered.

In the stage following the first mass sensor 2a, i.e., in the downstream of the first mass sensor 2a, the first chemical filter (the first filter) 34 is disposed. As the first chemical filter 34, for example, a chemical filter (Trade name: TIOS (registered trademark)-A) by Takasago Thermal Engineering Co., Ltd. can be used. Such chemical filter can adsorb the component of acid gas. The thickness of the first chemical filter 34 is, e.g., about 30 mm.

The first chemical filter 34 cannot always remove completely all the components of acid gas to be adsorbed. The first chemical filter 34 adsorbs the component of acid gas according to the adsorption ability.

In the present embodiment, the first chemical filter 34 adsorbs acid gas, but this is not essential. The kind of the first chemical filter 34 may be suitably selected according to a purpose.

In the stage following the first chemical filter 34, i.e., in the downstream of the first chemical filter 34, the second mass sensor 2b is disposed. As the second mass sensor 2b, the QCM sensor 2, for example, described above with reference to FIG. 1 can be used. On the surface of the second mass sensor 2b, various substances contained in the air which has passed through the chemical filter 34 can be adhered.

In the stage following the second mass sensor 2b, i.e., in the downstream of the second mass sensor 2b, the second chemical filter (the second filter) 38 is disposed.

As the second chemical filter 38, for example, a chemical filter which can adsorb the components of acid gas as does the first chemical filter 34 is used. As the second chemical filter 38, for example, a chemical filter (trade name: TIOS (registered trademark)-A) by Takasago Thermal Engineering Co., Ltd. is used, as is the first chemical filter 34. As the second chemical filter 38, a chemical filter whose thickness is smaller than the first chemical filter 34 is used. The thickness of the second chemical filter 38 is, e.g., about 10 mm. As the second chemical filter 38, a filter which is thinner than the first chemical filter 34 is used for the cost reduction.

As described above, the first chemical filter 34 cannot always adsorb completely all the components of acid gas to be adsorbed. The second chemical filter 38 adsorbs the components of the acid gas contained in the air which has pass through the first chemical filter 34 according to the absorption ability.

In the stage following the second chemical filter 38, i.e., in the downstream of the second chemical filter 38, the third mass sensor 2c is disposed. As the third mass sensor 2c, for example, the QCM sensor 2 described above with reference to FIG. 1 can be used. On the surface of the third mass sensor 2c, various substances contained in the air which has passed through the second chemical filter 38 can be adhered.

In the stage following the third mass sensor 2c, i.e., in the downstream of the third mass sensor 2c, the fan (air fluidizing means, atmosphere fluidizing means) 42 is disposed. The fan 42 is for fluidizing the atmosphere from the inlet 22 toward the outlet 24 (from the left side to the right side as viewed in FIG. 1).

In the atmospheric environment measuring apparatus according to the present embodiment, a control device 44 for generally controlling the atmospheric environment measuring apparatus is disposed. The control device 44 comprises a control unit 45 including a QCM controller (not illustrated), a CPU (not illustrated), etc., and a memory unit 46.

The QCM controller applies a prescribed voltage to the QCM sensor to resonate the QCM sensor to thereby measure a resonance frequency of the QCM sensor. As the QCM controller, for example, a mixed signal microcontroller (model number: MSP430F2274), etc., by Texas Instruments Incorporated is used.

The QCM controller is electrically connected to the respective mass sensors 2a-2c via interconnections 47a-47c. More specifically, the QCM controller is electrically connected to the terminals 16a, 16b of the respective mass sensors 2a-2c via the interconnections 47a-47c.

As the memory unit 46, a flash memory, for example, can be used.

The control unit 45 operates the fan 42 at a prescribed frequency to fluidize the atmosphere from the inlet 22 toward the outlet 24. The control unit 45 operates the mass sensors 2a-2c by using the QCM controller to measure resonance frequencies of the mass sensors 2a-2c.

The control unit 45 commands the memory unit 46 to store measured data together with measurement time data. The measured data contain data of resonance frequencies of the respective mass sensors 2a-2c. The measurement time data are data of measurement times at which the measured data were obtained.

The control device 44 can be operated with a battery (not illustrated), such as electric cells or others. The control device 44 can operate the mass sensors 2a-2c and the fan 42 with the battery.

The atmospheric environment measuring apparatus according to the present embodiment includes a transmission unit 48.

The transmission unit 48 can transmit and receive measured data and measurement time data mutually among other atmospheric environment measuring apparatus.

The transmission unit 48 can transmit measured data and measurement time data to a processing apparatus (monitor apparatus) 64 (see FIG. 3) disposed at a place remote from the atmospheric environment measuring apparatus via a wireless base station 62 (see FIG. 3) and a network 63 (see FIG. 3), such as an internet or others. As the transmission unit 48, for example, a wireless module (Trade name: Ibex) by AR'S Co. Ltd. can be used.

The transmission unit 48 can be operated with a battery, such as electric cells, or others.

Next, the operation of the atmospheric environment measuring apparatus according to the present embodiment will be described.

The control unit 45 of the control device 44 operates the fan 42 intermittently at a prescribed frequency. Specifically, the control unit 45 applies a voltage to the fan 42 at a prescribed frequency to thereby rotate the fan 42 for a prescribed period of time. The frequency of operating the fan 42 is, e.g., about once an hour. The one operation period of time is, e.g., about one minute.

The operation frequency and the operation period of time of the fan 42 are not limited to the above and can be suitably set.

When the fan 42 is operated, the atmosphere is fluidized in the casing 20 from the inlet 22 toward the outlet 24. The substances contained in the atmosphere can be adhered on the surface of the mass sensors 2a-2c.

On the surface of the first mass sensor 2a, the substances contained in the air which has not yet passed through the first chemical filer 34, i.e., the substances contained in the atmosphere can be adhered. On the surface of the second mass sensor 2b, the substance contained in the air which has passed through the first chemical filter 34 can be adhered. On the surface of the third mass sensor 2c, the substances contained in the air which has passed through the second chemical filter 38 can be adhered.

The measuring frequency of the resonance frequencies of the pass sensors 2a-2c is not limited to the above and can be suitably set.

The control unit 45 operates the respective mass sensors 2a-2c at a prescribed frequency by using the QCM controller (not illustrated). Specifically, the control unit 45 applies a prescribed voltage to the mass sensors 2a-2c by using the QCM controller to thereby resonate the mass sensors 2a-2c. The control unit 45 measures the resonance frequencies of the mass sensors 2a-2c by using the QCM controller. The frequency of the mass sensors 2a-2c measuring the resonance frequency is, e.g., about once an hour.

The control unit 45 stores the measured data of the resonance frequencies of the mass sensors 2a-2c together with the measurement time data in the memory unit 46.

The transmission unit 48 transmits the measured data, the measuring time data, etc. as follows.

As described above, in the present embodiment, the first mass sensor 2a is disposed in the stage previous to the first chemical filter 34 which can adsorb the components of acid gas, and in the stage following the first chemical filter 34, the second mass sensor 2b is disposed. Accordingly, on the first mass sensor 2a, the substances contained in the air whose components of acid gas have not been adsorbed is adhered. On the second mass sensor 2b, the substances contained in the air which has passed the first chemical filter 34 can be adhered. Thus, according to a concentration of the acid gas contained in the atmosphere, a difference takes place between the amount of change per unit time of the vibration frequency of the first mass sensor 2a and the amount of change per unit time of the vibration frequency of the second mass sensor 2b. Accordingly, in the present embodiment, based on the amount of change per unit time of the vibration frequency of the first mass sensor 2a and the amount of change per unit time of the vibration frequency of the second mass sensor 2b, a content level or a concentration of the acid gas contained in the atmosphere can be measured.

In the present embodiment, in the stage following the second mass sensor 2b, the second chemical filter 38 which can adsorb acid gas is disposed, and in the stage following the second chemical filter 38, the third mass sensor 2c is disposed. When the adsorption ability of the first chemical filter 34 lowers, the first chemical filter 34 cannot sufficiently adsorb the components of acid gas, and the components of the acid gas contained in the air which has passed the first chemical filter 34 can be adhered on the surface of the second mass sensor 2b. on the other hand, on the third mass sensor 2c, the substance contained in the air whose acid gas has been adsorbed by the second chemical filter 38 is adhered. Thus, according to a concentration of the acid gas contained in the air which has passed the first chemical filter 34, a difference takes place between the amount of change per unit time of the vibration frequency of the second mass sensor 2b and the amount of change per unit time of the vibration frequency of the third mass sensor 2c. Accordingly, it is also possible to judge that the the adsorption ability of the first chemical filter 34 has lowered based on the amount of changes per unit time of the vibration frequency of the first mass sensor 2a, the second mass sensor 2b and the third mass sensor 2c.

The atmospheric environment measuring apparatus according to the present embodiment can be driven by the battery. The atmospheric environment measuring apparatus according to the present embodiment has the simple constitution, which allows the atmospheric environment measuring apparatus to be inexpensively provided and to be less limited in the installation place. Accordingly, the atmospheric environment measuring apparatus according to the present embodiment can be installed in various places, in a large number and without large expenses.

(Atmospheric Environment Measuring System)

The atmospheric environment measuring system using the atmospheric environment measuring apparatus according to the present embodiment will be described with reference to FIGS. 2 and 3. FIG. 3 is the schematic view of the atmospheric environment measuring system according to the present embodiment.

Figure 3:
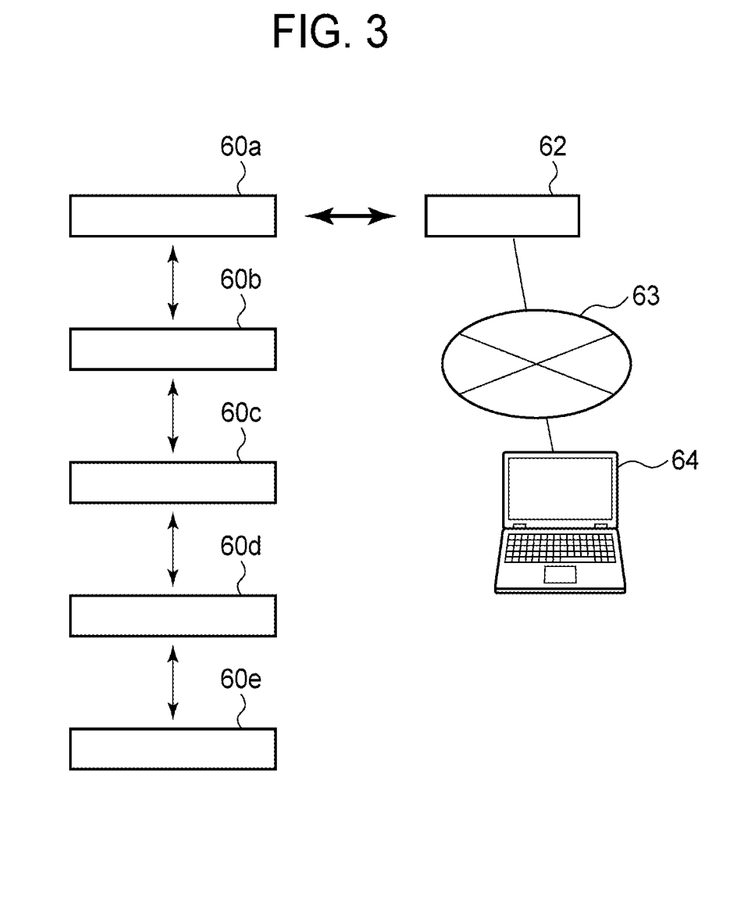
FIG. 3 is a schematic view of the atmospheric environment measuring system according to the first embodiment.

As illustrated in FIG. 3, the atmospheric environment measuring system according to the present embodiment comprises the atmospheric environment measuring apparatus 60a-60e, and a processing apparatus (monitoring apparatus) 64.

The atmospheric environment measuring apparatus 60a-60e can be the same as, e.g., the atmospheric environment measuring apparatus described above with reference to FIG. 2. The atmospheric environment measuring apparatus 60a-60e are installed in respective measurement places.

The atmospheric environment measuring apparatus 60a-60e can make wireless communication mutually via the respective transmission units 48 (see FIG. 2). The atmospheric environment measuring apparatus 60a-60e can make wireless communication via no access point, such as the base station 62, etc. (ad hock communication).

At least one of the atmospheric environment measuring apparatus 60a-60e is installed at a place where the atmospheric environment measuring apparatus can make wireless communication with the wireless base station (access point) 62. The atmospheric environment measuring system 60a will be described here by means of the example that at least the atmospheric environment measurement apparatus 60a is installed at a place where the atmospheric environment measuring apparatus 60a can make wireless communication with the wireless base station 62.

The wireless base station 62 is connected to the network 63, such as an internet or others.

The processing apparatus 64 is also connected to the network 63, such as a network or others.

As the processing apparatus 64, for example, a personal computer having a prescribed measurement program (monitor program), etc. installed can be used. The place where the processing apparatus 64 is installed may be a place where the processing apparatus 64 can be connected to the network 63. Accordingly, the processing apparatus 64 can be installed at a place far from the atmospheric environment measuring apparatus 60a-60e. Thus, according to the present embodiment the atmospheric environments can be measured at remote places.

Next, the operation of the atmospheric environment measuring system according to the present embodiment will be described with reference to FIG. 3.

The operation will be described here by means of the example that the wireless communication is made between the atmospheric environment measuring apparatus 60a and the wireless base station 62 but is not made between the atmospheric environment measuring apparatus 60b-60e and the wireless base station 62.

The atmospheric environment measuring apparatus 60a-60e installed at respective measurement places obtain measured data at a prescribed frequency, as described above.

The measured data measured by the respective atmospheric environment measuring apparatus 60a-60e are aggregated in the atmospheric environment measuring apparatus 60a. Specifically, measured data, measurement time data and identification data (identification information, ID numbers) of the atmospheric environment measuring apparatus which have obtained the measured data are aggregated in the atmospheric environment measuring apparatus 60a by the respective atmospheric environment measuring apparatus 60a-60e mutually making wireless communication.

The atmospheric environment measuring apparatus 60a transmits the measured data, measurement time data and the identification data of the atmospheric environment measuring apparatus which have obtained the measured data to the processing apparatus 64 via the wireless base station 62 and the network 63.

The processing apparatus 64 measures (monitors) the atmospheric environment as will be described below, based on the measured data and measurement time data obtained by the respective atmospheric environment measuring apparatus 60a-60e.

As described above, in the present embodiment, the measured data, etc. obtained by the atmospheric environment measuring apparatus 60a-60e installed respective measurement places are transmitted to the processing apparatus 64 via the wireless communication and the network 63. Thus, according to the present embodiment, the atmospheric environment measuring apparatus 60a-60e can be installed at various measurement places and measure atmospheric environments at remote places.

(Atmospheric Environment Measuring Method)

Figure 4:
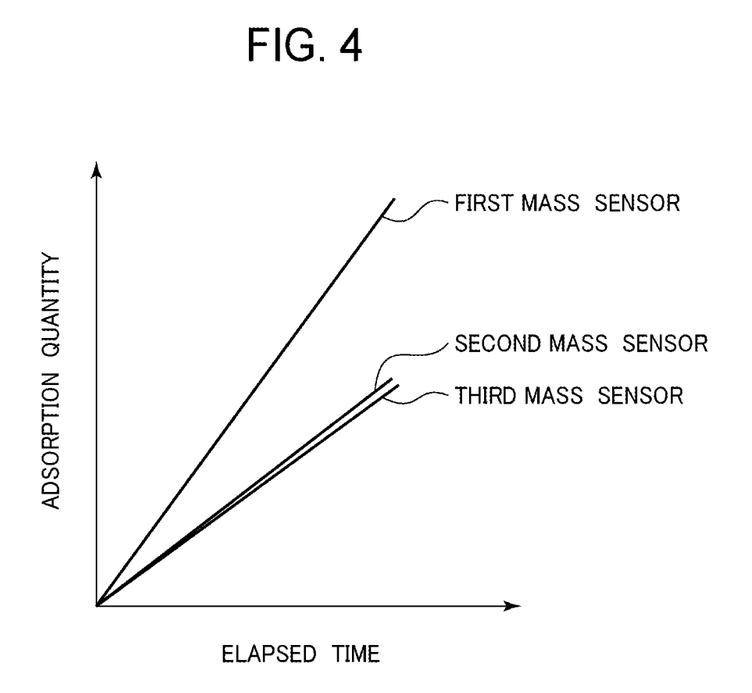
FIG. 4 is a graph illustrating changes of mass of adhesion of substances on respective mass sensors when adsorption ability of a first chemical filter is sufficient.
Figure 5:
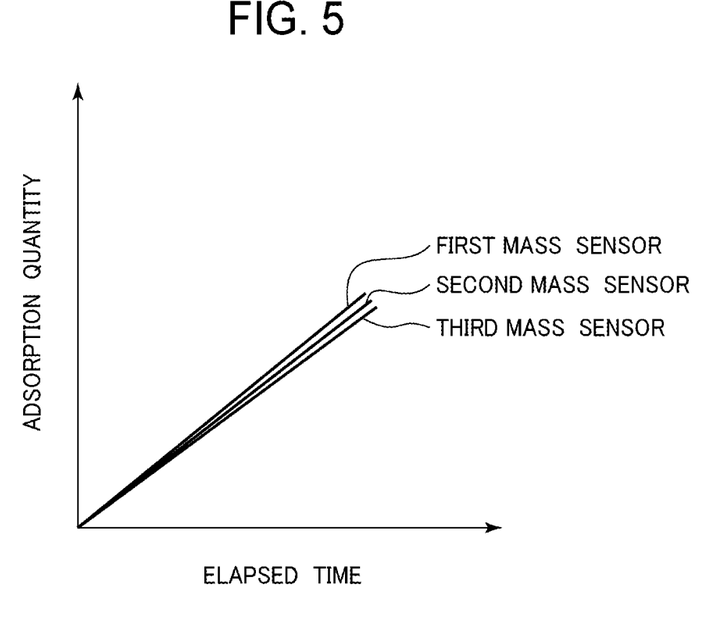
FIG. 5 is a graph illustrating changes of mass of adhesion of the substances on the respective mass sensors when no acid gas is present in atmosphere.
Figure 6:
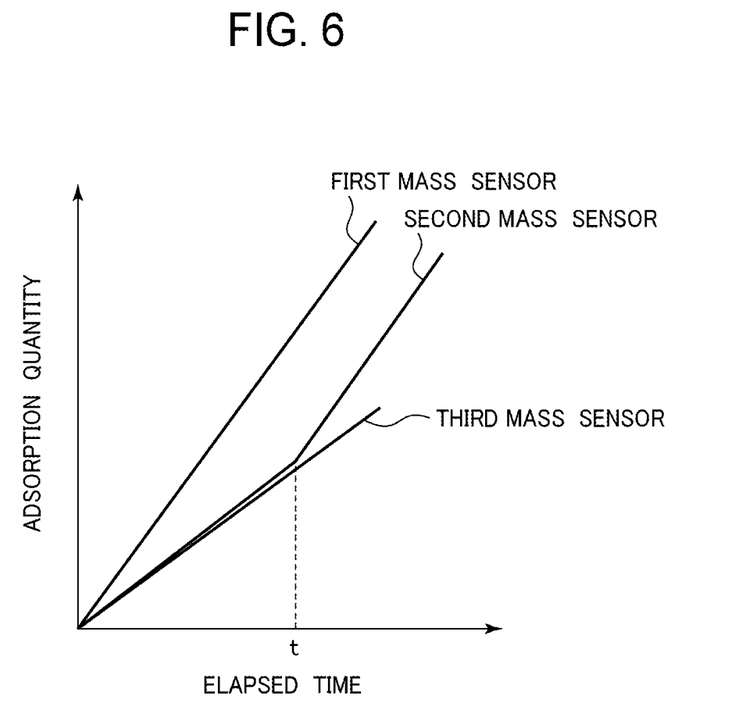
FIG. 6 is a graph illustrating changes of mass of adhesion of the substances on the respective mass sensors when the first chemical filter is broken through during a measurement.

The atmospheric environment measuring method using the atmospheric environment measuring apparatus according to the present embodiment will be described with reference to FIGS. 3 to 6. FIG. 4 is the graph of changes of the adsorption quantity of substances on the respective mass sensors 2a-2c when adsorption ability of a first chemical filter is sufficient. FIG. 5 is the graph of changes of mass of adhesion of the substances on the respective mass sensors 2a-2c when no acid gas is present in atmosphere. FIG. 6 is a graph of changes of the adsorption quantity of the substances on the respective mass sensors 2a-2c when the first chemical filter 34 is broken through during a measurement.

First, as described above, the respective atmospheric environment measuring apparatus 60a-60e measure the resonance frequencies of the mass sensors 2a-2c at a prescribed frequency. The obtained measured data are transmitted to the processing apparatus 64 via the network 63 or others together with the measurement time data, the identification data of the atmospheric environment measuring apparatus 60a-60e which have made the measurement.

As described above, the measurement program (monitor program) for measuring (monitoring) the atmospheric environment is installed in the processing apparatus 64. The processing apparatus 64 measures the atmospheric environment as follows using the measurement program.

Based on the measured data of the first mass sensor 2a and the measured data of the second mass sensor 2b, the processing apparatus 64 can measure the content level of the acid gas in the atmosphere as exemplified below.

That is, processing apparatus 64 gives the amount of change per unit time of the resonance frequency of the first mass sensor 2a. The amount of change per unit time of the resonance frequency of the first mass sensor 2a can be given based on the measured data of the resonance frequency of the first mass sensor 2a and the measurement time data when the measurement was made.

The processing apparatus 64 give the amount of change per unit time of the resonance frequency of the second mass sensor 2b. The amount of change per unit time of the resonance frequency of the second mass sensor 2b can be given based on the measured data of the resonance frequency of the second mass sensor 2b and the measurement time data when the measurement was made.

When the adsorption ability of the first chemical filter 34 is sufficient, the adsorption quantity of a substance on the surfaces of the respective mass sensors 2a-2c change as exemplified in FIG. 4. The second mass sensor 2b is disposed in the stage following the chemical filter 34 which can adsorb acid gas, and accordingly, the adsorption quantity of the substance on the surface of the first sensor 2a is larger by a concentration of the acid gas contained in the atmosphere than an adsorption quantity of the substance on the surface of the second mass sensor 2b.

As described above, the amount of changes of the resonance frequency of the respective mass sensors 2a-2b are proportional to the amount of changes of the masses of a substance adhered on the surface of the mass sensors 2a-2c. Accordingly, a difference between the amount of change per unit time of the resonance frequency of the first mass sensor 2a and the amount of change per unit time of the resonance frequency of the second mass sensor 2b is proportional to a concentration of the acid gas contained in the atmosphere.

However, it is not always easy to compute the concentration of acid gas contained in the atmosphere, based on a difference between the amount of change per unit time of the resonance frequency of the first mass sensor 2a and the amount of change per unit time of the resonance frequency of the second mass sensor 2b.

Then, in the present embodiment, a reference data (training data) is prepared in advance. Such reference data is stored in a memory (not illustrated) as of hard disc drive (HDD) or others installed in the processing apparatus 64.

Such reference data was prepared by, e.g., experimentally giving a difference between the amount of change per unit time of the resonance frequency of the first mass sensor 2a and the amount of change per unit time of the resonance frequency of the second mass sensor 2b for respective concentrations of acid gas.

Accordingly, the concentration of acid gas can be determined by comparing the difference between the amount of change per unit time of the resonance frequency of the first mass sensor 2a and the amount of change per unit time of the resonance frequency of the second mass sensor 2b with the reference data which is given for each concentrations of acid gas.

The method has been described here by means of the example that the concentration of acid gas is determined but is not limited to determining the concentration. The method is applicable widely in determining levels of the acid gas contained in the atmosphere.

For example, differences between the amount of change per unit time of the resonance frequency of the first mass sensor 2a and the amount of change per unit time of the resonance frequency of the second mass sensor 2b are given for respective content levels of the acid gas contained in the atmosphere. As the levels of the acid gas contained in the atmosphere, Level 1, Level 2, . . . , etc., for examples are considered.

A difference between the amount of change per unit time of the resonance frequency of the first mass sensor 2a and the amount of change per unit time of the resonance frequency of the second mass sensor 2b is compared with the reference data, whereby the content level of the acid gas contained in the atmosphere can be given.

As described above, the atmospheric environment measuring method according to the present embodiment can determine a content level of acid gas contained in the atmosphere.

In the present embodiment, a place where acid gas has been generated can be also identified.

That is, in the present embodiment, the atmospheric environment measuring apparatus 60a-60e are respectively installed in respected measurement places.

The method will be described by means of the example that five atmospheric environment measuring apparatus are installed, but the number of the atmospheric environment measuring apparatus is not limited to five, and the atmospheric environment measuring apparatus may be suitably installed at places where the atmospheric environment is to be measured.

For example, it is assumed that the content level of acid gas contained in the atmosphere is relatively high in the measured data given by the atmospheric environment measuring apparatus 60c.

On the other hand, it is assumed that the content levels of the acid gas contained in the atmosphere are relatively low in the measured data given by the atmospheric environment measuring apparatus 60a, 60b, 60d, 60e.

In this case, it can be judged that there is the possibility that the acid gas is being generated near the atmospheric environment measuring apparatus 60c.

For example, in the case that the atmospheric environment measuring apparatus 60a-60e are installed at respective places of a volcano, it can be judged that acid gas is being generated near the place where the atmospheric environment measuring apparatus 60c is installed. In this case, the processing apparatus 64 can output an alarm that acid gas is generated near the place where the atmospheric environment measuring apparatus 60c is installed.

As described above, the atmospheric environment measuring method according to the present embodiment can contributes to identifying the generation place of acid gas, etc.

When the chemical filter is continuously used for a long period of time, the adsorption ability of the chemical filter lowers. The chemical filter ending the lifetime is called breakthrough.

In the atmospheric environment measuring method according to the present embodiment, the breakthrough of the first chemical filter 34 is judged as follows.

When the first chemical filter 34 has come to be broken through, the acid gas in the atmosphere is not adsorbed by the first chemical filter 34. Accordingly, the amount of change per unit time of the resonance frequency of the first mass sensor 2a and the amount of change per unit time of the resonance frequency of the second mass sensor 2b become equal to each other.

However, the breakthrough of the first chemical filter 34 cannot be judged, only based on that the amount of change per unit time of the resonance frequency of the first mass sensor 2a and the amount of change per unit time of the resonance frequency of the second mass sensor 2b having come to be equal to each other. This is because, as illustrated in FIG. 5, when no acid gas is contained in the atmosphere, a change of the adsorption quantity of a substance on the surface of the first mass sensor 2a and a change of the adsorption quantity of the substance on the surface of the second mass sensor 2b become equal to each other.

Then, in the present embodiment, the measured data of the third mass sensor 2c, which is disposed in the stage following the second chemical filter 38 is used to thereby judge the breakthrough of the first chemical filter 34.

When the first chemical filter 34 has come to break through, as described above, the amount of change per unit time of the resonance frequency of the first mass sensor 2a and the amount of change per unit time of the resonance frequency of the second mass sensor 2b becomes equal to each other. This is because, as illustrated in FIG. 6, after a time t when the second chemical filter 38 has been broken through, a change of the adsorption quantity of a substance on the surface of the first mass sensor 2a becomes equal to a change of the adsorption quantity of the substance on the surface of the second mass sensor 2b.

With the first chemical filter 34 broken through, when acid gas is contained in the atmosphere, the amount of change per unit time of the resonance frequency of the third mass sensor 2c becomes smaller than the amount of changes per unit time of the resonance frequency of the first and the second mass sensor 2a, 2b.

For the following reason, the amount of change per unit time of the resonance frequency of the third mass sensor 2c becomes smaller than the amount of changes per unit time of the resonance frequency of the first and the second mass sensors 2a, 2b. That is, deterioration of the chemical filter advances from the upstream. When the first chemical filter 34 has been broken through, the second chemical filter 38 has not yet been broken through. The third mass sensor 2c is disposed in the stage following the second chemical filter 38 which has not yet been broken through. Accordingly, as illustrated in FIG. 6, a change of the adsorption quantity of a substance on the surface of the third mass sensor 2c is smaller than changes of the adsorption quantities of the substance on the surface of the first and the second mass sensors 2a, 2b. Thus, the amount of change per unit time of the resonance frequency of the third mass sensor 2c becomes smaller than the amounts of changes per unit time of the resonance frequency of the first and the second mass sensors 2a, 2b.

In this case, it can be judged that the first chemical filter 34 has been broken through.

That is, when the first condition and the second condition as follows are both satisfied, it can be judged that the first chemical filter 34 has been broken through. The first condition is that the amount of change per unit time of the resonance frequency of the first mass sensor 2a is substantially equal to the amount of change per unit time of the resonance frequency of the second mass sensor 2b. The second condition is that the amount of change per unit time of the resonance frequency of the third mass sensor 2c is smaller by a prescribed value than the amount of change per unit time of the resonance frequency of the second mass sensor 2b.

The atmospheric environment measuring method has been described by means of the example that the first chemical filter 34 has been broken through. However, it may be judged that the adsorption ability of the first chemical filter 34 has lowered before the adsorption ability of the chemical filter 34 is completely lost.

Before the adsorption ability of the first chemical filter 34 has been completely lost, in the case that acid gas is contained in the atmosphere, the amount of change per unit time of the resonance frequency of the second mass sensor 2b becomes smaller than the amount of change per unit time of the resonance frequency of the first mass sensor 2a. This is because the acid gas is adsorbed to some extent by the first chemical filter 34. In this case, the amount of change per unit time of the resonance frequency of the third mass sensor 2c becomes smaller than the amount of change per unit time of the resonance frequency of the second mass sensor 2b. This is because the acid gas is adsorbed by the second chemical filter 38.

Accordingly, when any one of the first condition and the second condition to be described below is satisfied, it can be judged that the adsorption ability of the first chemical filter 34 has lowered to some extent. The first condition is that the amount of change per unit time of the resonance frequency of the second mass sensor 2b is smaller by the first prescribed value than the amount of change per unit time of the resonance frequency of the first mass sensor 2a. The second conditions is that the amount of change per unit time of the resonance frequency of the second mass sensor 2b is larger by the second prescribed vale than the amount of change per unit time of the resonance frequency of the third mass sensor 2c.

As described above, according to the present embodiment, the degradation of the adsorption ability of the first chemical filter 34 can be judged.

As described above, according to the present embodiment, the content level of the acid gas contained in the atmosphere can be measured.

According to the present embodiment, the degradation of the adsorption ability of the first chemical filter 34 and the breakthrough thereof can be judged, whereby erroneous measurements, etc. can be prevented.

As described above, according to the present embodiment, the first chemical filter 34 may be replaced in accordance with the degradation of the adsorption ability of the first chemical filter 34 or its breakthrough, which can also make the replacement of the first chemical filter 34 less frequent.

[b] Second Embodiment

Figure 7:
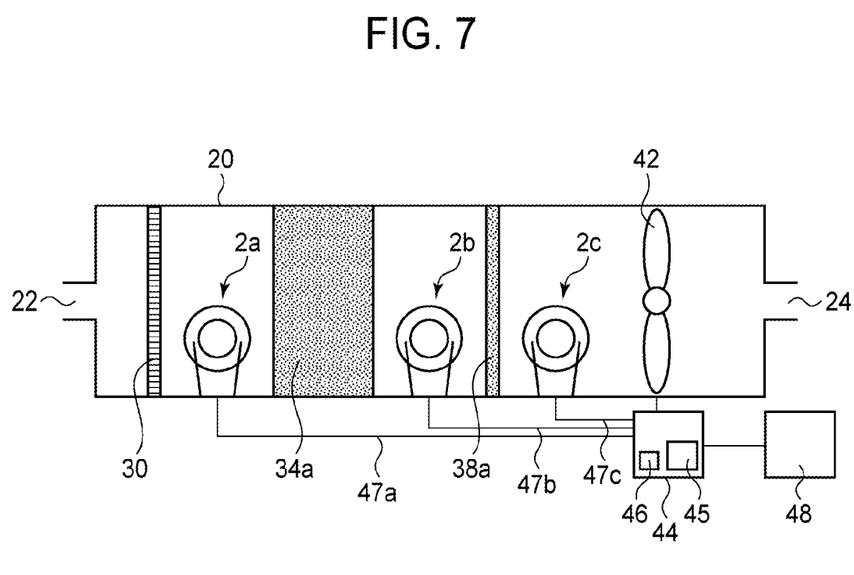
FIG. 7 is a view illustrating a construction of an atmospheric environment measuring apparatus according to a second embodiment.
Figure 8:
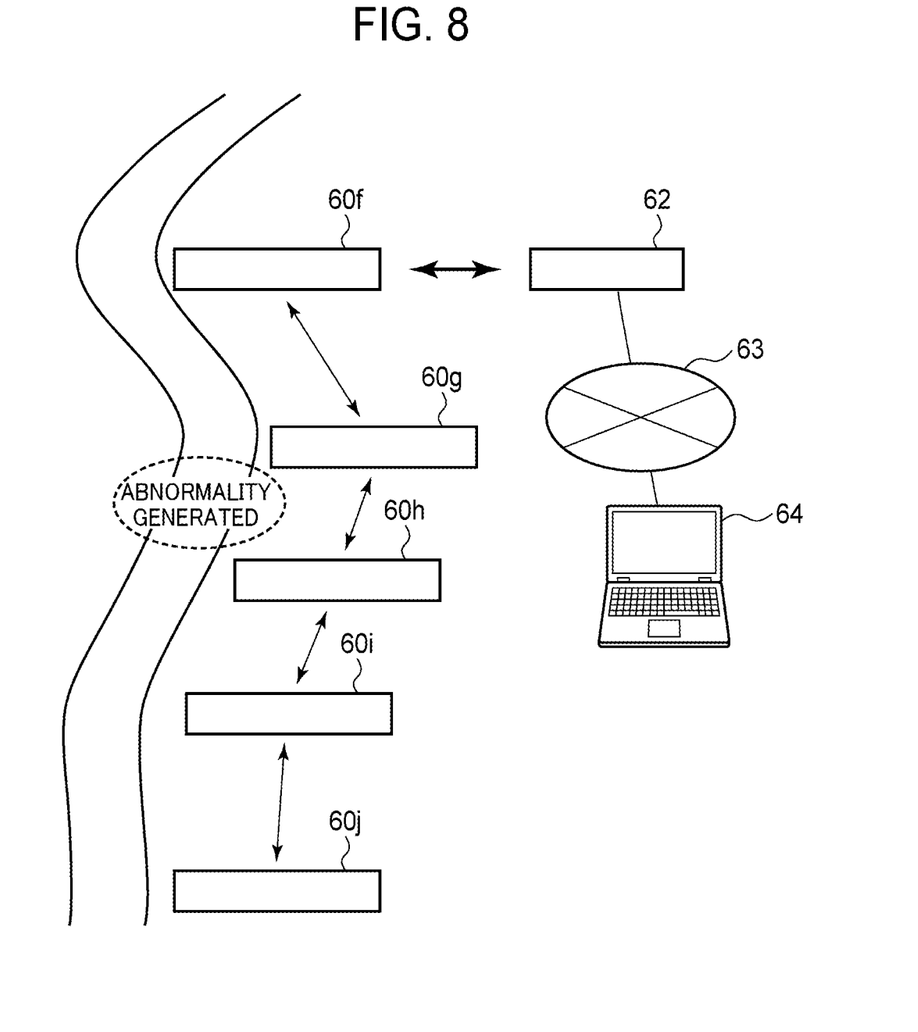
FIG. 8 is a schematic view illustrating an atmospheric environment measuring system according to the second embodiment.

The atmospheric environment measuring apparatus, the atmospheric environment measuring method and the atmospheric environment measuring system according to a second embodiment will be described with reference to FIGS. 7 and 8. FIG. 7 is the view illustrating the construction of the atmospheric environment measuring apparatus according to the present embodiment. FIG. 8 is the schematic view of the atmospheric environment measuring system according to the present embodiment. The same members of the atmospheric environment measuring apparatus and the atmospheric environment measuring method and the atmospheric environment measuring system according to the first embodiment are represented by the same reference numbers not to repeat or to simplify the description.

In the atmospheric environment measuring apparatus, the atmospheric environment measuring method and the atmospheric environment measuring system according to the present embodiment, the gas to be detected is basic gas.

First, the atmospheric environment measuring apparatus according to the present embodiment will be described with reference to FIG. 7.

In the atmospheric environment measuring apparatus according to the present embodiment, as the first chemical filter 34a, a chemical filter which can adsorb basic gas is used.

As such chemical filter, for example, a chemical filter (Trade name: TIOS (registered trademark)-B) by Takasago Thermal Engineering Co., Ltd. or others can be used.

Also as the second chemical filter 38a, a chemical filter which can adsorb basic gas is used. As such chemical filter, the chemical filter (Trade name: TIOS (registered trademark)-B) by Takasago Thermal Engineering Co., Ltd. or others can be also used. The thickness of the second chemical filter 38a is set smaller than the thickness of the first chemical filter 34a, as in the first embodiment.

As described above, the atmospheric environment measuring apparatus according to the present embodiment is constituted.

The atmospheric environment measuring method according to the present embodiment is substantially the same as the atmospheric environment measuring method according to the first embodiment and will not be described.

As described above, according to the present embodiment, as the chemical filters 34a, 34b, the chemical filter which can adsorb basic gas is used, the atmospheric environment measurement for basic gas as the gas to be detected can be made.

Next, the atmospheric environment measuring system according to the present embodiment will be described with reference to FIG. 8.

As illustrated in FIG. 8, the atmospheric environment measuring apparatus 60f-60j are installed at respective places along a river As the atmospheric environment measuring apparatus 60f-60j, the atmospheric environment measuring apparatus according to the present embodiment described above with reference to FIG. 7 can be used.

For example, it is assumed that the content level of basic gas contained in the atmosphere is relatively high in the measured data given by the atmospheric environment measuring apparatus 60g, 60h.

On the other hand, the content level of the basic gas contained in the atmosphere was relatively low in the measured data given by the atmospheric environment measuring apparatus 60f, 60i, 60j.

In this case, it can be judged that the basic gas is being generated (abnormality generated) near the places where the atmospheric environment measuring apparatus 60g, 60h are installed. In this case, the processing apparatus 64 can generate an alarm that basic gas is being generated near the places where the atmospheric environment measuring apparatus 60g, 60h are installed.

Amine-based gas is emitted from dead fishes. Amine-based gas is one of basic gas. Accordingly, according to the present embodiment, a mass death of fishes, etc. can be detected indirectly by basic gas. By detecting a mass death of fishes, etc., pollution of rivers, etc. can be indirectly detected.

As described above, the present embodiment can contribute to identifying generation places of basic gas, and thus can contribute to identifying the source of pollution, etc., of the river, etc.

Modified Embodiments

The present invention is not limited to the above-described embodiment and can cover other various modifications.

For example, the first embodiment has been described by means of the example that the gas to be detected is acid gas, and the second embodiment has been described by means of the example that the gas to be detected is basic gas. However, the gas to be detected is not limited to them. For example, the gas to be detected may be organic gas. When the gas to be detected is organic gas, as the chemical filters 34, 38, a filter which can adsorb organic gas is used. As the chemical filter which can adsorb organic gas can be, e.g., a chemical filter (Trade name: TIOS (registered trademark)-O) by Takasago Thermal Engineering Co., Ltd.

The above-described embodiments have been described by means of the example that the content level or the concentration of a gas to be detected contained in the atmosphere is detected by using the processing apparatus 64. The content level or the concentration may not be essentially judged by the processing apparatus 64. For example, the content level or the concentration of a gas to be detected contained in the atmosphere may be judged by the control unit 45 of the control apparatus 44 of the atmospheric environment measuring apparatus.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An atmospheric environment measuring apparatus comprising:
    a first filter disposed in a casing and adsorbing a component of a gas to be detected;
    a first mass sensor disposed in the casing between an inlet of the casing and the first filter, including a first piezoelectric vibration element and changing a resonance frequency according to a mass of a substance adhered on a surface of the first piezoelectric vibration element;
    a second mass sensor disposed in a stage following the first filter in the casing, including a second piezoelectric vibration element and changing a resonance frequency according to a mass of a substance adhered on a surface of the second piezoelectric vibration element;
    a second filter disposed in a stage following the second mass sensor in the casing and adsorbing a component of the gas to be detected;
    a third mass sensor disposed in a stage following the second filter in the casing, including a third piezoelectric vibration element and changing a resonance frequency according to a mass of a substance adhered on a surface of the third piezoelectric vibration element; and
    a fan disposed in a stage following the third mass sensor in the casing and fluidizing atmosphere from the inlet toward an outlet of the casing, wherein
    degradation of an adsorption ability of the first filter is judged based on the amount of change per unit time of the measured data given by the first mass sensor, the amount of change per unit time of the measured data given by the second mass sensor and an amount of change per unit time of the measured data given by the third mass sensor.

2. The atmospheric environment measuring apparatus according to claim 1, further comprising
    a control unit intermittently operating the first mass sensor, the second mass sensor, the third mass sensor and the fan respectively.

3. The atmospheric environment measuring apparatus according to claim 1, further comprising a transmission unit wirelessly transmitting measured data given by the first mass sensor, the second mass sensor and the third mass sensor.

4. An atmospheric environment measuring system comprising:
an atmospheric environment measuring apparatus including a first filter disposed in a casing and adsorbing a component of a gas to be detected; a first mass sensor disposed in the casing between an inlet of the casing and the first filter, including a first piezoelectric vibration element and changing a resonance frequency according to a mass of a substance adhered on a surface of the first piezoelectric vibration element; a second mass sensor disposed in a stage following the first filter in the casing, including a second piezoelectric vibration element and changing a resonance frequency according to a mass of a substance adhered on a surface of the second piezoelectric vibration element; a second filter disposed in a stage following the second mass sensor in the casing and adsorbing a component of the gas to be detected; a third mass sensor disposed in a stage following the second filter in the casing, including a third piezoelectric vibration element and changing a resonance frequency according to a mass of a substance adhered on a surface of the third piezoelectric vibration element; a fan disposed in a stage following the third mass sensor in the casing and fluidizing atmosphere from the inlet toward an outlet of the casing; and a transmission unit wirelessly transmitting measured data given by the first mass sensor and the second mass sensor; and
a processing apparatus obtaining the measured data transmitted from the atmospheric environment measuring apparatus via a network and measuring an atmospheric environment based on the measured data, wherein
degradation of an adsorption ability of the first filter is judged based on the amount of change per unit time of the measured data given by the first mass sensor, the amount of change per unit time of the measured data given by the second mass sensor and an amount of change per unit time of the measured data given by the third mass sensor.

5. An atmospheric environment measuring method using an atmospheric environment measuring apparatus including a first filter disposed in a casing and adsorbing a component of a gas to be detected; a first mass sensor disposed in the casing between an inlet of the casing and the first filter, including a first piezoelectric vibration element and changing a resonance frequency according to a mass of a substance adhered on a surface of the first piezoelectric vibration element; a second mass sensor disposed in a stage following the first filter in the casing, including a second piezoelectric vibration element and changing a resonance frequency according to a mass of a substance adhered on a surface of the second piezoelectric vibration element; a second filter disposed in a stage following the second mass sensor in the casing and adsorbing a component of the gas to be detected; a third mass sensor disposed in a stage following the second filter in the casing, including a third piezoelectric vibration element and changing a resonance frequency according to a mass of a substance adhered on a surface of the third piezoelectric vibration element; and a fan disposed in a stage following the second mass sensor in the casing and fluidizing atmosphere from the inlet toward an outlet of the casing,
wherein a content level or a concentration of the gas to be detected in the atmosphere is determined based on measured data by the first mass sensor and measured data by the second mass sensor, and
wherein degradation of an adsorption ability of the first filter is judged based on the amount of change per unit time of the measured data given by the first mass sensor, the amount of change per unit time of the measured data given by the second mass sensor and an amount of change per unit time of the measured data given by the third mass sensor.

6. The atmospheric environment measuring method according to claim 5, wherein
the content level or the concentration of the gas to be detected in the atmosphere is measured based on a difference between an amount of change per unit time of the measured data given by the first mass sensor and an amount of change per unit time of the measured data given by the second mass sensor.

7. The atmospheric environment measuring method according to claim 5, wherein
the adsorption ability of the first filter is judged to have been lost when the amount of change per unit time of the measured data given by the first mass sensor and the amount of change per unit time of the measured data given by the second mass sensor are equal to each other, and the amount of change per unit time of the measured data given by the third mass sensor is smaller than both the amount of change per unit time of the measured data given by the first mass sensor and the amount of change per unit time of the measured data given by the second mass sensor.

8. The atmospheric environment measuring method according to claim 5, wherein
the first mass sensor, the second mass sensor and the fan are respectively operated intermittently.

9. The atmospheric environment measuring method according to claim 5, wherein
the atmospheric environment measuring apparatus further comprises a transmission unit wirelessly transmitting the measured data given by the first mass sensor and the measured data given by the second mass sensor, and
the measured data given by the first mass sensor and the measured data given by the second mass sensor transmitted by the transmission unit of the atmospheric environment measuring apparatus are obtained via a network, and the content level or the concentration of the gas to be detected in the atmosphere is determined based on the measured data given by the first mass sensor and the measured data given by the second mass sensor.

* * * * *